United States Patent [19]

Peake

[11] Patent Number: 5,801,337

[45] Date of Patent: Sep. 1, 1998

[54] METHOD OF AND APPARATUS FOR COMPENSATING FOR LOAD/ ENVIRONMENT TEMPERATURE DIFFERENTIAL-INDUCED MEASURED LOAD WEIGHT ERROR

[75] Inventor: Steven C. Peake, Dubuque, Iowa

[73] Assignee: Barnstead/Thermolyne Corporation, Dubuque, Iowa

[21] Appl. No.: 584,313

[22] Filed: Jan. 11, 1996

[51] Int. Cl.[6] .......................... G01G 9/00; G01G 19/22; G01N 25/00

[52] U.S. Cl. .............. 177/1; 177/25.13; 177/50; 73/1.13; 436/908; 374/14

[58] Field of Search .............. 177/50, 245, 25.11, 177/25.12, 25.13, 25.19, 25.14, 1; 73/1 B, 1.13; 364/568, 503, 571.03; 374/14; 436/908, 155, 160

[56] References Cited

U.S. PATENT DOCUMENTS

| | | | |
|---|---|---|---|
| 3,813,918 | 6/1974 | Moe | 374/14 |
| 3,890,825 | 6/1975 | Davis | 374/14 |
| 3,916,670 | 11/1975 | Davis et al. | 374/14 |
| 4,165,633 | 8/1979 | Raisanen | 73/76 |
| 4,291,775 | 9/1981 | Collins | 177/1 |
| 4,874,950 | 10/1989 | Regimand | 250/390.04 |
| 4,889,201 | 12/1989 | Oldendorf et al. | 177/25.14 |
| 4,964,734 | 10/1990 | Yoshida et al. | 374/14 |
| 5,058,422 | 10/1991 | Shimauchi et al. | 73/1 B |
| 5,081,046 | 1/1992 | Schneider | 436/139 |
| 5,085,527 | 2/1992 | Gilbert | 374/14 |
| 5,279,971 | 1/1994 | Schneider | 436/139 |
| 5,308,931 | 5/1994 | Griffen | 177/25.14 |
| 5,321,634 | 6/1994 | Obata et al. | 364/568 X |
| 5,625,170 | 4/1997 | Poris | 177/50 |

*Primary Examiner*—Hezron E. Williams
*Assistant Examiner*—Randy W. Gibson
*Attorney, Agent, or Firm*—Wood, Herron & Evans

[57] ABSTRACT

A method of compensating for load/environment temperature differential-induced measured load weight error comprises the steps of: providing a load having a load temperature $T_L$; providing an environment having an environment temperature $T_E$, different from the load temperature; subjecting the load to the environment at time $t_0$; measuring the weight $w_0$ of the load at time $t_0$; measuring the weight $w_1$ of the load at time $t_1$; and calculating the change in weight $\Delta w_{td}$ of the load, between the time $t_0$ at which the load is subjected to the environment and the time $t_2$ at which the load and environment temperatures reach equilibrium, induced by the temperature differential between the load and the environment, from the measured load weights $w_0$ and $w_1$. The method further comprises the steps of: measuring the weight $w_n$ of the load at time $t_n \geq t_2$; and subtracting the temperature differential-induced load weight change $\Delta w_{td}$ from the load weight $w_n$. Also provided is apparatus for determining the binder content of a sample of building material by weighing the sample before combustion, combusting the binder from the balance of the sample, and weighing the sample after combustion.

17 Claims, 3 Drawing Sheets

METHOD OF AND APPARATUS FOR COMPENSATING FOR LOAD/ENVIRONMENT TEMPERATURE DIFFERENTIAL-INDUCED MEASURED LOAD WEIGHT ERROR

FIELD OF THE INVENTION

This invention relates generally to weighing samples or loads, and more particularly to weighing samples or loads accurately when the load is at one temperature and the environment in which the load is being weighed is at another temperature. One specific application of the present invention is in the area of asphalt ashing furnaces where a building material, i.e. paving material, has a binder content, typically asphalt, which is determined by weighing the sample before and after combustion of the asphalt binder from the sample.

BACKGROUND OF THE INVENTION

The weight of an object is a function of the temperature differential between the object's temperature and the temperature of the object's surroundings. This phenomenon is readily demonstrated by heating an object to a relatively higher temperature than its surrounding or ambient temperature, placing the object on a balance scale and observing the displayed object's weight as the object cools to an equilibrium temperature with the ambient temperature. The object's weight displayed on the balance will increase as its temperature decreases in route to reaching the ambient temperature.

This temperature differential-induced weight change is caused by the air flow patterns around and above the object or load as its temperature changes. Initially, the air is turbulent and rises rapidly off of the load which is then hotter than the surrounding air creating a low pressure area above the load thus creating "lift" and causing the load to weigh "light" initially. As the load temperature decreases the rising air becomes less turbulent therefore causing less "lift" on the load. Once equilibrium is reached, there ceases to be any low pressure area above the load. Thus the "equilibrium weight" of the load is heavier than the light initial weight.

By the same token, when a cooler load is placed in a hotter environment, the falling air creates a high pressure area above the load thus causing the load to weigh "heavy" initially. Once equilibrium is reached, there ceases to be any high pressure area above the load. Thus the "equilibrium weight" of the load is lighter than the heavy initial weight.

The degree to which the load/environment temperature differential effects the load weight is a function of a number of factors. The surface area of the load affects the rate at which the load temperature changes since the temperature change is based primarily on convective heat gain. The area covered affects the lift on the load. The heat capacity of the material being tested will also affect the weight versus time curve since a material with a very high heat capacity will change temperature more slowly than a load of a material with a lower heat capacity, in the same environment. The properties of convective loss of the surface of the load will affect the rate at which the load changes weight with temperature.

One application where the above described load/environment temperature differential-induced measured load weight error poses problems is in the area of asphalt ashing furnaces. Road or highway paving material is generally required to be a certain percentage by weight binder. Typical is the requirement that the material contain 6% by weight asphalt. The typical allowable variation is on the order of ±0.2%. However, the temperature differential-induced measured load weight error can, in some cases, use up most, if not all, of this allowable variation.

More particularly, a typical paving material sample of which the binder content is to be determined is on the order of about 1200 grams. A typical weight loss due to combustion or burning off of the binder is on the order of about 70 grams. Thus the weight percentage of binder, or asphalt, in the paving material is simply the starting weight, 1200 grams, less the weight of the sample after combustion of the asphalt, or 1130 grams, which equals a weight decrease of the above-mentioned 70 grams or a 5.83% by weight asphalt content.

A typical temperature differential-induced measured load weight error of the initial weight of a 1200 gram sample can be on the order of approximately 2 grams, in the case of a pre-dried paving material sample which is at about 300 degrees F. placed into an ashing furnace which is at about 1000 degrees F. In other words, the balance scale of the furnace will indicate that by the time the sample temperature rises to reach equilibrium with the furnace temperature, the load will have "lost" 2 grams of weight, even though the 2 gram weight loss is not attributable to asphalt being combusted from the sample. Thus the scale, at completion of combustion of the asphalt, will indicate a weight loss of 72 grams (instead of 70 grams), which calculates out to be 6.00% by weight asphalt content. Thus, the entire allowable variation of ±0.2% is practically used up by the temperature differential-induced measured load weight error, leaving essentially no margin of error for other error inducing factors in the process.

Complicating matters is the fact that there is not a discrete point at which the asphalt and oven reach equilibrium before combustion of the asphalt begins. This is because temperature equilibrium between the asphalt and oven takes on the order of 12 to 13 minutes, but the asphalt begins to combust at about 5 minutes. Thus it is impossible to determine the temperature differential-induced measured load weight error by merely subtracting the initial load weight from the final equilibrium load weight (at 12 to 13 minutes).

It is therefore one objective of the present invention to provide a method of compensating for load/environment temperature differential-induced measured load weight error.

It is another objective of the present invention to provide a method of determining the binder content of a sample of building material by combusting the binder from the balance of the sample in a furnace, including compensating for sample/furnace temperature differential-induced measured sample weight error.

It is yet another objective of the present invention to provide apparatus for carrying out the above method of determining the binder content of a sample of building material including compensating for sample/furnace temperature differential-induced measured sample weight error.

SUMMARY OF THE INVENTION

The present invention attains the stated objectives by providing a method of compensating for load/environment temperature differential-induced measured load weight error. The method comprises the steps of: providing a load having a load temperature $T_L$; providing an environment having an environment temperature $T_E$, different from the load temperature; subjecting the load to the environment at time $t_0$; measuring the weight $w_0$ of the load at time $t_0$; measuring the weight $w_1$ of the load at time $t_1$; and calculating the change in weight $\Delta w_{td}$ of the load, between the time $t_0$ at which the load is subjected to the environment and the time $t_2$ at which the load and environment temperatures reach equilibrium, induced by the temperature differential between the load and the environment, from the measured load weights $w_0$ and $w_1$. The method further comprises the steps of: measuring the weight $w_n$ of the load at time $t_n \geq t_2$; and subtracting the temperature differential-induced load weight change $\Delta w_{td}$ from the load weight $w_n$.

In the preferred form of this aspect of the present invention, the method comprises: providing a load having a load temperature $T_L$; providing an environment having an environment temperature $T_E$, different from the load temperature; subjecting the load to the environment at time $t_0$; measuring the weight $w_0$ of the load at time $t_0$; measuring the weight $w_1$ of the load at time $t_1$; measuring the weight $w_2$ of the load at time $t_2$; and calculating the change in weight $\Delta w_{td}$ of the load, between the time $t_0$ at which the load is subjected to the environment and the time $t_3$ at which the load and environment temperatures reach equilibrium, induced by the temperature differential between the load and the environment, from the measured load weights $w_1$, and $w_2$.

In another aspect of the present invention, there is provided a method of determining the binder content of a sample of building material by combusting the binder from the balance of the sample in a furnace, including compensating for sample/furnace temperature differential-induced measured sample weight error. This method comprises the steps of: providing a sample of building material having a sample temperature $T_s$ and containing an amount of binder to be determined; providing a furnace having a furnace temperature $T_F$, different from the sample temperature; placing the sample into the furnace at time $t_0$; measuring the initial weight $w_0$ of the sample at time $t_0$; measuring the weight $w_1$ of the sample at time $t_1$; calculating the change in weight $\Delta w_{td}$ of the sample, between the time $t_0$ at which the sample is placed into the furnace and the time $t_2$ at which the sample and furnace temperatures reach equilibrium, induced by the temperature differential between the sample and the furnace, from the measured sample weights $w_0$ and $w_1$; combusting substantially entirely all the binder from the sample; measuring the residual weight $w_3$ of the sample at time $t_3$; and subtracting the temperature differential-induced sample weight change $\Delta w_{td}$ from the difference between the sample residual weight $w_3$ and the sample initial weight $w_0$ to produce a compensated sample weight change $\Delta w_c$ indicative of the sample binder content.

In the preferred form of this aspect of the present invention the method comprises: providing a sample of building material having a sample temperature $T_s$ and containing an amount of binder to be determined; providing a furnace having a furnace temperature $T_F$, different from the sample temperature; placing the sample into the furnace at time $t_0$; measuring the initial weight $w_0$ of the sample at time $t_0$; measuring the weight $w_1$, of the sample at time $t_0$; measuring the weight $w_2$ of the sample at time $t_2$; calculating the change in weight $\Delta w_{td}$ of the sample, between the time $t_0$ at which the sample is placed into the furnace and the time $t_3$ at which the sample and furnace temperatures reach equilibrium, induced by the temperature differential between the sample and the furnace, from the measured sample weights $w_1$, and $w_2$; combusting substantially entirely all the binder from the sample; measuring the residual weight $w_4$ of the sample at time $t_4$; and subtracting the temperature differential-induced sample weight change $\Delta w_{td}$ from the difference between the sample residual weight $w_4$ and the sample initial weight $w_0$ to produce a compensated sample weight change $\Delta w_c$ indicative of the sample binder content.

This method further comprises the step of calculating the change in weight $\Delta w_{td}$ according to the relationship: $\Delta w_{td} = 2w_1 + 3(w_2 - w_1)$; where $t_1 = 1$ minute, and $t_2 = 2$ minutes.

The present invention also provides apparatus for determining the binder content of a sample of building material by weighing the sample before combustion, combusting the binder from the balance of the sample, and weighing the sample after combustion. The apparatus comprises: a furnace for insertion of the sample thereinto and for combusting substantially entirely all the binder from the sample; a scale for measuring the weight of the sample in the furnace at discrete time intervals; means for calculating the change in weight of the sample between the time at which the sample is placed into the furnace and the time at which the sample and the furnace temperatures reach equilibrium, induced by the temperature differential between the sample and the furnace, from at least two measured sample weights made prior to the time at which the sample and the furnace temperatures reach equilibrium; the means for calculating subtracting the change in weight of the sample induced by the temperature differential from the total change in weight of the sample between the time the sample is placed into the furnace and the time at which combustion of the binder is substantially complete to produce a compensated sample weight change indicative of the sample binder content; and a display for displaying the binder content.

The means for calculating the change in weight of the sample between the time at which the sample is placed into the furnace and the time at which the sample and the furnace temperatures reach equilibrium, induced by the temperature differential between the sample and the furnace, calculates the change in weight according to the relationship: $\Delta w_{td} = 2w_1 + 3(w_2 - w_1)$; where $\Delta w_{td}$ is the temperature differential-induced sample weight change, $t_1$ is 1 minute from the time the sample is placed into said furnace, $t_2$ is 2 minutes from the time the sample is placed into said furnace, $w_1$ is the sample weight at $t_1$, and $w_2$ is the sample weight at $t_2$.

One advantage of the present invention is that a method of compensating for load/environment temperature differential-induced measured load weight error is provided.

Another advantage of the present invention is that a method of determining the binder content of a sample of building material by combusting the binder from the balance of the sample in a furnace, including compensating for sample/furnace temperature differential-induced measured sample weight error, is provided.

Yet another advantage of the present invention is that apparatus for carrying out the above method of determining the binder content of a sample of building material including compensating for sample/furnace temperature differential-induce measured sample weight error is provided.

These and other objects and advantages of the present invention will become more readily apparent during the following detailed description taken in conjunction with the drawings herein, in which:

DETAILED DESCRIPTION OF THE INVENTION

Figure 1:
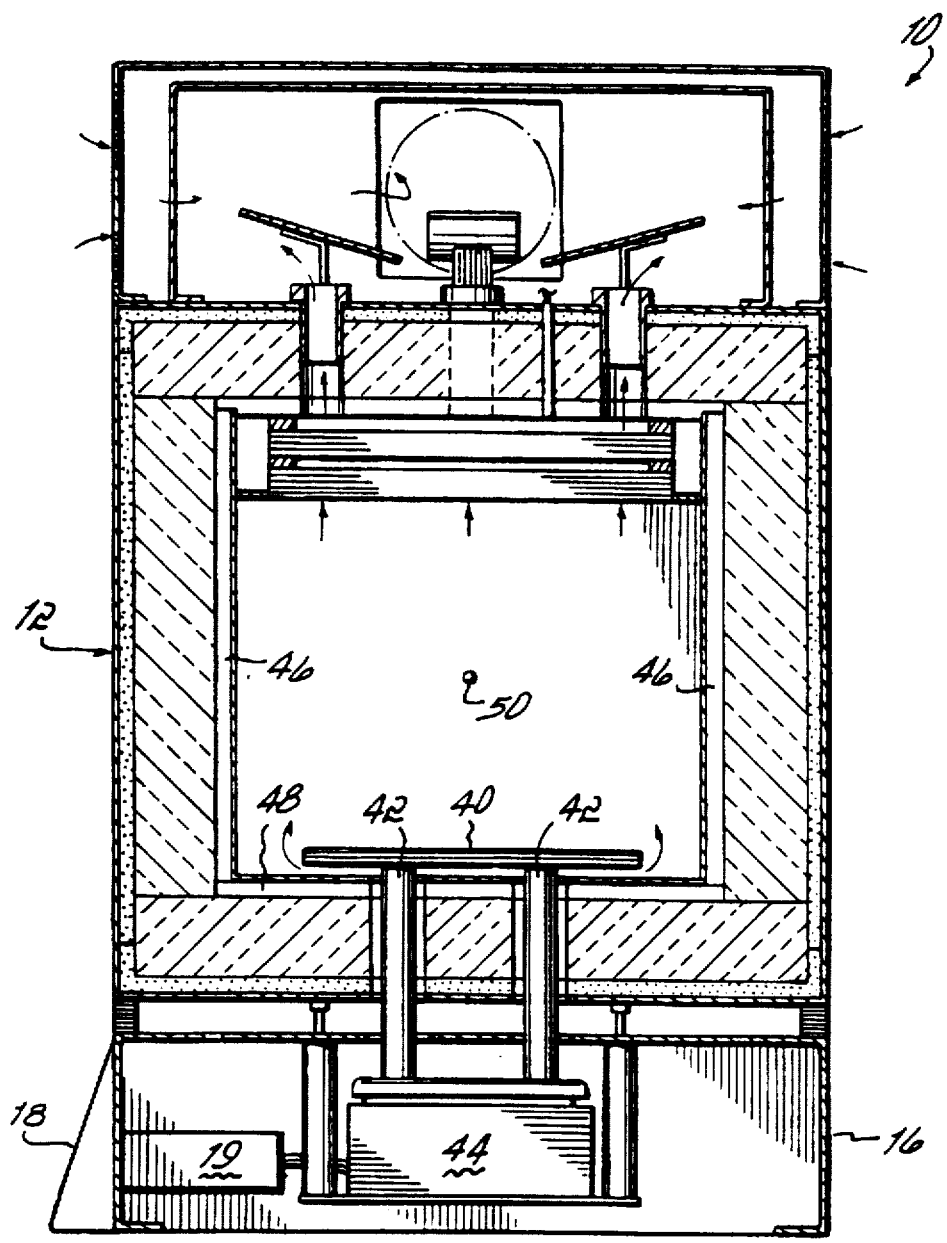
FIG. 1 is a schematic view of an asphalt ashing furnace which operates according to the principles of the present invention.

Referring first to FIG. 1, there is illustrated in schematic form an ashing furnace 10 which operates according to the principles of the present invention. Ashing furnace 10 is generally of the form of the type disclosed in co-pending patent application Ser. No. 08/355,914 filed Dec. 14, 1994, assigned to the assignee of the present invention and hereby incorporated by reference herein as if fully set forth in its entirety.

Ashing furnace 10 includes an enclosure 12 atop a base 16 including an operator input and display panel 18 for entry of data to ashing furnace 10 and for display of weight information, and housing a controller 19 for controlling the operation of the furnace 10.

A hearth plate 40 is disposed within the interior of the enclosure 12 and is for supporting a specimen thereatop. Hearth plate 40 is supported atop four posts 42 which themselves are supported atop a weigh scale 44 which provides a readout on panel 18 of the weight of the specimen supported atop the hearth plate 40 during combustion. Heater plates such as side wall heater plates 46,46, and bottom wall heater plate 48 provide furnace heat. Thermocouple 50 is mounted within the enclosure and senses the temperature in the area in the furnace 10 adjacent a specimen supported atop the hearth plate. Thermocouple 50 transmits signals to the controller 19, which includes a suitable microprocessor programmed with appropriate software, for example proportional integral derivative ("PID") software, which maintains the temperature of the heater plates 46, 48 at a preselected temperature. For typical asphalt ashing applications, the operating temperatures in the furnace are on the order of 300 degrees C. to 600 degrees C.

The microprocessor of the controller 19 is programmed so as to factor out the load or sample apparent weight "loss" between the time the sample is placed into the furnace 10, at which time the sample is pre-dried and at a temperature of approximately 300 degrees F., and the time at which the sample temperature reaches equilibrium with the furnace temperature of approximately 1000 degrees F., typically a duration of 12 to 14 minutes. Empirical testing has shown that if the weight of the load is sampled twice after first being introduced into the furnace 10, the change in weight of the sample between the time at which the sample is placed into the furnace and the time at which the sample and furnace temperatures reach equilibrium, induced by the temperature differential between the sample and the furnace, may be calculated from those two weight readings and then subtracted from the weight of the sample after substantially all of the binder of the sample has been combusted to provided a compensated weight change of the sample which is more accurate. Initially, the falling air currents above the cooler load in a hotter environment create a high pressure area over the load causing the load to "weigh heavy". Once equilibrium is reached and there is no more high pressure area over the load, the load weighs lighter than the initial heavy weight, thus an apparent weight loss. The algorithm was developed by observing the early (i.e. within the first two minutes) trend of weight versus time versus the total final weight change of the load once equilibrium was reached (at about 12–14 minutes).

Figure 2:
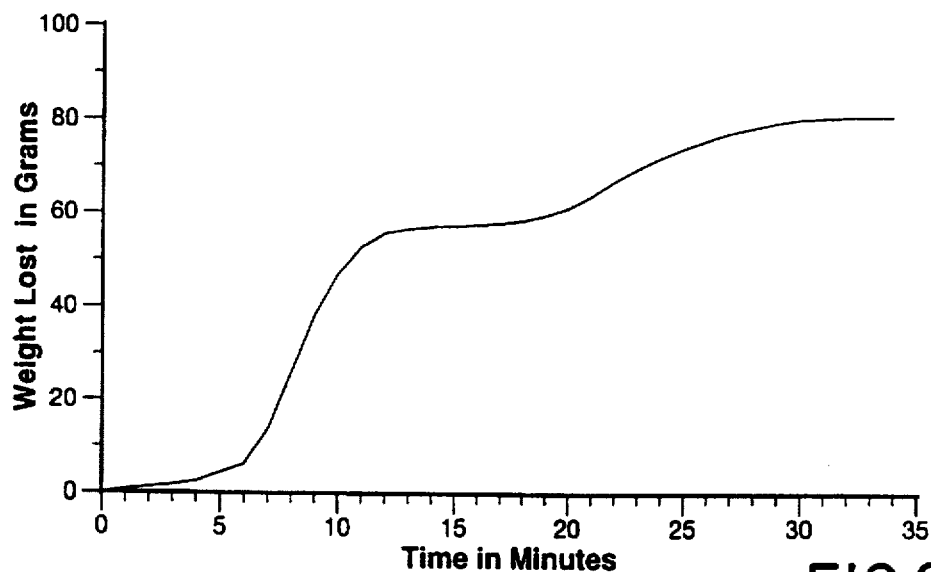
FIG. 2 is a graph of weight lost versus time for a typical asphalt road paving sample.
Figure 3:
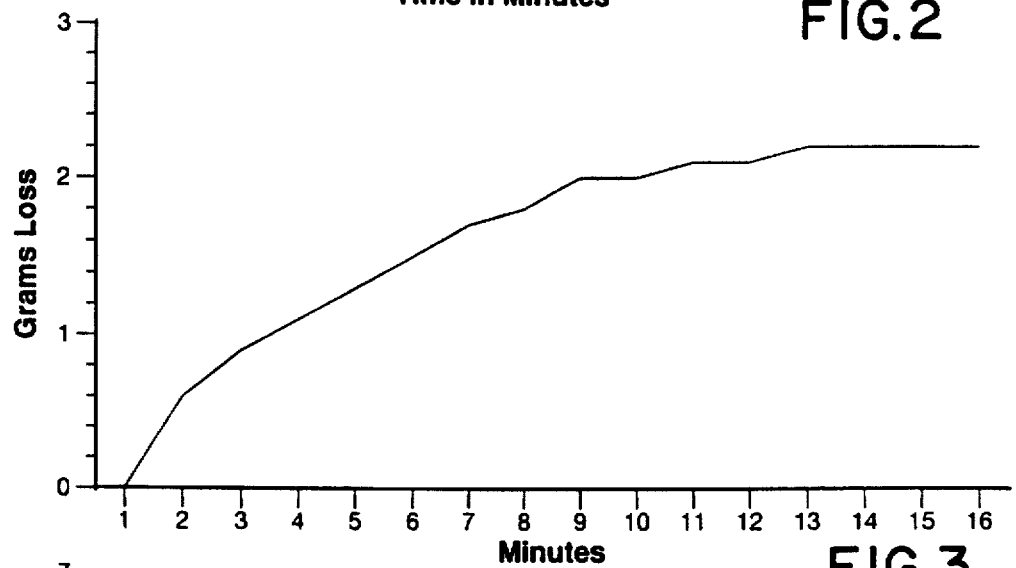
FIG. 3 is a graph of weight lost versus time for a noncombustible "dummy" load.
Figure 4:
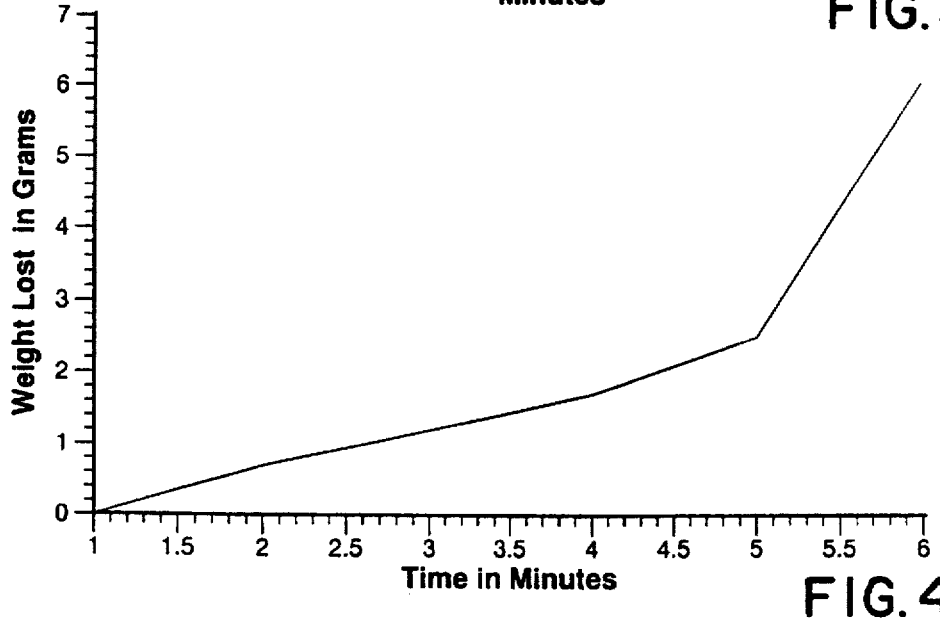
FIG. 4 is an enlarged graph of the first 6 minutes of FIG. 2.

Referring to FIG. 2, the weight lost in grams versus time in minutes is plotted for a sample asphalt construction material load. This plot includes weight "lost" due to reaching asphalt/oven equilibrium as well as due to combustion of asphalt from the load. FIG. 3 is a plot of the weight lost in grams versus time for a non-combustible "dummy" load having the same general physical characteristics as discussed above, for example, size, shape etc., as the asphalt load of FIG. 2. The dummy load could be, for example, stainless steel balls or screws of the same weight and volume as the paving material sample or pre-burned granite. As is seen in FIG. 3, the temperature differential-induced measured load weight error is on the order of about 2 grams and is reached at about 12 to 13 minutes. FIG. 4 is an enlargement of the first 6 minutes of the FIG. 2 graph. As can be seen, at about 5 minutes the combustion of the asphalt begins to have a significant effect on the weight loss, long before equilibrium is reached at 12–13 minutes.

Figures 5, 6:
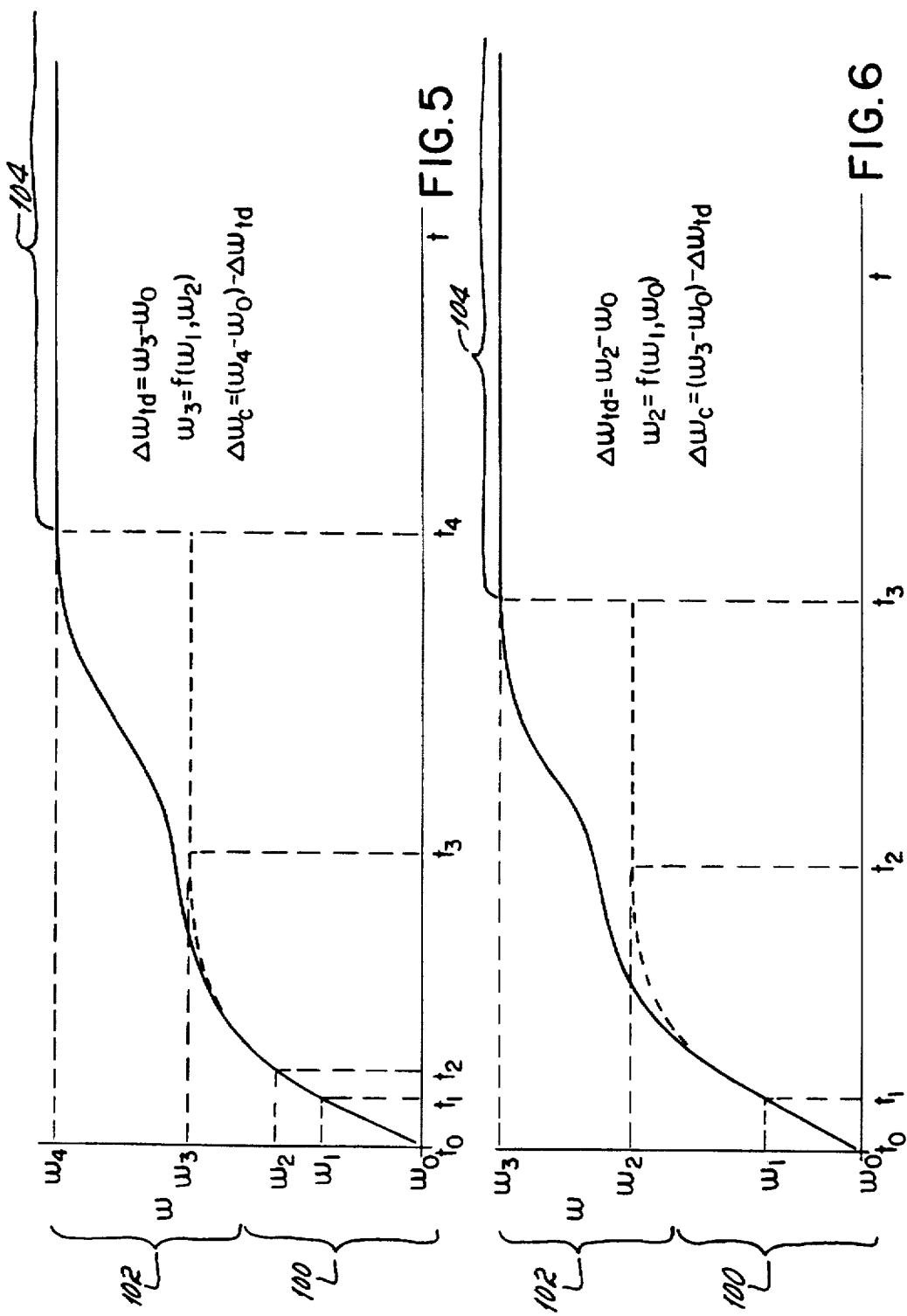
FIG. 5 is a curve (not to scale) of sample weight loss versus time and illustrating the preferred methodology of the present invention.
FIG. 6 is a curve (not to scale) similar to FIG. 2 illustrating another version of the methodology of the present invention.

More particularly, and referring to FIG. 5 now, the weight w of a sample is shown plotted versus time t. Region 100 illustrates the time during which the sample or load temperature $T_L$ is rising to reach that of the furnace or environment $T_E$ and during which there is no combustion of asphalt. Region 102 illustrates the time during which the sample temperature continues to rise to reach that of the oven and combustion of the sample binder occurs, and region 104 illustrates the sample weight after substantially all of the binder has been combusted from the sample.

As shown on the figure, $w_3-w_0=\Delta w_{td}$, the change in weight of the sample between the time $t_0$ at which the load is subjected to the environment and the time $t_3$ at which the load and environment temperatures reach equilibrium, induced by the temperature differential between the load and the environment. As briefly discussed above, $w_3$ may be defined empirocally as a function of $w_1$, and $w_2$, or $w_3=f(w_1,w_2)$. After substantially all of the binder has been combusted from the sample at time $t_4$ to produce a residual sample weight of $w_4$, then, the compensated sample weight change $\Delta w_c=(w_4-w_0)-\Delta w_{td}$. Empirical testing has shown that, for paving material samples of the type used to test the binder content thereof, $\Delta w_{td}=2w_1+3(w_2-w_1)$, where $t_1=1$ minute, and $t_2=2$ minutes. Thus the total temperature differential-induced sample weight change can be predicted or extrapolated from the two weight readings. Other empirical relationships can of course be developed for other load types.

While it is preferred for accuracy purposes to take two weight readings at 1 minute intervals after insertion of the sample into the furnace, one can use the initial weight of the sample $w_0$ and the weight of the sample $w_1$ after the first 1 minute interval to calculate the weight $w_2$ of the sample at the time the sample and furnace temperatures reach equilibrium at time $t_2$. This is illustrated in FIG. 6. The calculation then proceeds as above but with only one weight reading having been taken. After substantially all of the binder has been combusted from the sample at time $t_3$ to produce a residual sample weight of $w_3$, then, the compensated sample weight change $\Delta w_c=(w_3-w_0)-\Delta w_{td}$, where $\Delta w_{td}=2w_0+3(w_1-w_0)$, and where $t_1=1$ minute. While some accuracy may be compromised, such a modification of the above described method is nonetheless contemplated as being within the scope of the present invention.

The present invention also has applications other than sample binder determinations which would not involve combusting a portion of the sample. In those cases, and referring still to FIG. 3, all that would need to be done is to measure the weight $w_n$ of the load at some time $t_n \geq t_2$ and then subtract the temperature differential-induced load weight change $\Delta w_{td}$ from the load weight $w_n$ to produce a compensated weight. Similarly, with respect to the FIG. 2 technique, all that would need to be done is to measure the weight $w_n$ of the load at time $t_n \geq t_3$ and then subtract the temperature differential-induced load weight change $\Delta w_{td}$ from the load weight $w_n$.

The present invention also has application in a moisture content evaluation process where it is desired to determine the moisture content of a load or sample. In a moisture content evaluation, the time frame for sampling the load weight would have to be much shorter, on the order of 10 to 15 seconds, as opposed to 2 minutes as described.

The microprocessor 19 could also be programmed with a "self-learning" algorithm which could determine the appropriate compensation algorithm for use with many different load types. For example a user would select a different load size and shape, and would place a dummy load into the furnace 10 which has substantially the same size and shape characteristics as the new load (and which is also substantially moisture-free). The furnace would monitor the dummy load weight "loss" through the time it takes the load to reach equilibrium with the furnace temperature, and after, e.g., three trial runs, a curve fitting algorithm would calculate the compensation algorithm for use with the new load. The equation would be similar to that described above but the multiplication factors would be variables which the system would calculate and store based on the data collected from the three test runs. The concept would be similar to an adaptive control algorithm used in temperature controllers where the history is used to calculate the PID values used to control the furnace.

Those skilled in the art will readily recognize numerous adaptations and modifications which can be made to the present invention which will result in an improved method of compensating for load/environment temperature differential-induced measured load weight error, yet all of which will fall within the spirit and scope of the present invention as defined in the following claims. Accordingly, the invention is to be limited only by the scope of the following claims and their equivalents.

What is claimed is:

1. A method of compensating for load/environment temperature differential-induced measured load weight error comprising the steps of:

providing a load having a load temperature $T_L$;

providing an environment having an environment temperature $T_E$, different from the load temperature;

providing processor;

providing a weighing device;

subjecting the load to the environment at time $t_0$;

measuring with the weighing device the weight $w_0$ of the load at time $t_0$;

measuring with the weighing device the weight $w_1$ of the load at time $t_1$;

calculating with the processor the apparent change in weight $\Delta w_{td}$ of the load, between the time $t_0$ at which the load is subjected to the environment and the time $t_2$ at which the load and environment temperatures reach equilibrium, induced solely by the temperature differential between the load and the environment, from the measured load weights $w_0$ and $w_1$; and generating a signal with the processor representative of the change in weight $\Delta w_{td}$.

2. The method of claim 1 further comprising the steps of:

measuring the weight $w_n$ of the load at time $t_n \geq t_2$; and subtracting the temperature differential-induced load weight change $\Delta w_{td}$ from the load weight $w_n$.

3. A method of compensating for load/environment temperature differential-induced measured load weight error comprising the steps of:

providing a load having a load temperature $T_L$;

providing an environment having an environment temperature $T_E$, different from the load temperature;

providing a processor;

providing a weighing device;

subjecting the load to the environment at time $t_0$;

measuring with the weighing device the weight $w_0$ of the load at time $t_0$;

measuring with the weighing device the weight $w_1$ of the load at time $t_1$;

measuring with the weighing device the weight $w_2$ of the load at time $t_2$;

calculating with the processor the apparent change in weight $\Delta w_{td}$ of the load, between the time $t_0$ at which the load is subjected to the environment and the time $t_3$ at which the load and environment temperatures reach equilibrium, induced solely by the temperature differential between the load and the environment, from the measured load weights $w_1$ and $w_2$; and generating a signal with the processor representative of the change in weight $\Delta w_{td}$.

4. The method of claim 3 further comprising the steps of:

measuring the weight $w_n$ of the load at time $t_n \geq t_3$; and subtracting the temperature differential-induced load weight change $\Delta w_{td}$ from the load weight $w_n$.

5. A method of determining the binder content of a sample of building material by combusting the binder from the balance of the sample in a furnace, including compensating for sample/furnace temperature differential-induced measured sample weight error, comprising the steps of:

providing a sample of building material having a sample temperature $T_s$, and containing an amount of binder to be determined;

providing a furnace having a furnace temperature $T_F$, different from the sample temperature;

providing a processor;

providing a weighing device;

placing the sample into the furnace at time $t_0$;

measuring with the weighing device the initial weight $w_0$ of the sample at time $t_0$;

measuring with the weighing device the weight $w_1$ of the sample at time $t_1$;

calculating with the processor the apparent change in weight $\Delta w_{td}$ of the sample, between the time $t_0$ at which the sample is placed into the furnace and the time $t_2$ at which the sample and furnace temperatures reach equilibrium, induced solely by the temperature differential between the sample and the furnace, from the measured sample weights $w_0$ and $w_1$;

combusting with the furnace substantially entirely all the binder from the sample;

measuring with the weighing device the residual weight $w_3$ of the sample at time $t_3$;

subtracting with the processor the temperature differential-induced sample weight change $\Delta w_{td}$ from the difference between the sample residual weight $w_3$ and the sample initial weight $w_0$ to produce a compensated sample weight change $\Delta w_c$ indicative of the sample binder content; and generating a signal with the processor representative of the compensated sample weight change $\Delta w_{td}$.

6. A method of determining the binder content of a sample of building material by combusting the binder from the balance of the sample in a furnace, including compensating for sample/furnace temperature differential-induced measured sample weight error, comprising the steps of:

providing a sample of building material having a sample temperature $T_s$ and containing an amount of binder to be determined;

providing a furnace having a furnace temperature $T_F$, different from the sample temperature;

providing processor;

providing weighing device:

placing the sample into the furnace at time $t_0$;

measuring with the weighing device the initial weight $w_0$ of the sample at time $t_0$;

measuring with the weighing device the weight $w_1$ of the sample at time $t_1$;

measuring with the weighing device the weight $w_2$ of the sample at time $t_2$;

calculating with the processor the apparent change in weight $\Delta w_{td}$ of the sample, between the time $t_0$ at which the sample is placed into the furnace and the time $t_3$ at which the sample and furnace temperatures reach equilibrium, induced solely by the temperature differential between the sample and the furnace, from the measured sample weights $w_1$ and $w_2$;

combusting with the furnace substantially entirely all the binder from the sample;

measuring with the weighing device the residual weight $w_4$ of the sample at time $t_4$;

subtracting with the processor the temperature differential-induced sample weight change $\Delta w_{td}$ from the difference between the sample residual weight $w_4$ and the sample initial weight $w_0$ to produce a compensated sample weight change $\Delta w_c$ indicative of the sample binder content; and generating a signal with the processor representative of the compensated sample weight change $\Delta w_{td}$.

7. The method of claim 6 wherein the step of calculating the change in weight $\Delta w_{td}$ is calculated according to the relationship:

$\Delta w_{td}=2w_1+3(w_2-w_1)$; where $t_1=1$ minute, and $t_2=2$ minutes.

8. Apparatus for determining the binder content of a sample of building material by weighing the sample before combustion, combusting the binder from the balance of the sample, and weighing the sample after combustion, comprising:

a furnace for insertion of the sample thereinto and for combusting substantially entirely all the binder from the sample;

a scale for measuring the weight of the sample in said furnace at discrete time intervals;

means for calculating the apparent change in weight of the sample between the time at which the sample is placed into said furnace and the time at which the sample and said furnace temperatures reach equilibrium, induced solely by the temperature differential between the sample and said furnace, from at least two measured sample weights made prior to the time at which the sample and said furnace temperatures reach equilibrium;

said means for calculating also for subtracting the change in weight of the sample induced by the temperature differential from the total change in weight of the sample between the time the sample is placed into said furnace and the time at which combustion of the binder is substantially complete to produce a compensated sample weight change indicative of the sample binder content; and means for displaying the binder content.

9. The apparatus of claim 8 wherein said means for calculating the change in weight of the sample between the time at which the sample is placed into said furnace and the time at which the sample and said furnace temperatures reach equilibrium, induced by the temperature differential between the sample and said furnace, calculates the change in weight according to the relationship:

$\Delta w_{td}=2w_1+3(w_2-w_1)$; where $\Delta w_{td}$ is the temperature differential-induced sample weight change, $t_1$ is 1 minute from the time the sample is placed into said furnace, $t_2$ is 2 minutes from the time the sample is placed into said furnace, $w_1$ is the sample weight at $t_1$, and $w_2$ is the sample weight at $t_2$.

10. Apparatus for determining the binder content of a sample of building material by weighing the sample before combustion, combusting the binder from the balance of the sample, and weighing the sample after combustion, comprising:

a furnace for insertion of the sample thereinto and for combusting substantially entirely all the binder from the sample;

a scale for measuring the weight of the sample in said furnace at discrete time intervals;

a processor for calculating the apparent change in weight of the sample between the time at which the sample is placed into said furnace and the time at which the sample and said furnace temperatures reach equilibrium, induced solely by the temperature differential between the sample and said furnace, from at least two measured sample weights made prior to the time at which the sample and said furnace temperatures reach equilibrium;

said processor also for substracting the change in weight of the sample induced by the temperature differential from the total change in weight of the sample between the time the sample is placed into said furnace and the time at which combustion of the binder is substantially complete to produce a compensated sample weight change indicative of the sample binder content; and a display for displaying the binder content.

11. The apparatus of claim 10 wherein said means for calculating the change in weight of the sample between the time at which the sample is placed into said furnace and the time at which the sample and said furnace temperatures reach equilibrium, induced by the temperature differential between the sample and said furnace, calculates the change in weight according to the relationship:

$\Delta w_{td} = 2w_1 + 3(w_2 - w_1)$; where $\Delta w_{td}$ is the temperature differential-induced sample weight change.

$t_1$ is 1 minute from the time the sample is placed into said furnace.

$t_2$ is 2 minutes from the time the sample is placed into said furnace.

$w_1$ is the sample weight at $t_1$. and $w_2$ is the sample weight at $t_2$.

12. A method of compensating for load/environment temperature differential-induced measured load weight error comprising the steps of:

providing a load having a load temperature $T_L$;

providing an environment having an environment temperature $T_E$, different from the load temperature;

providing a processor;

providing a weighing device;

subjecting the load to the environment at time $t_0$;

measuring with the weighing device the weight $w_0$ of the load at time $t_0$;

measuring with the weighing device the weight $w_1$ of the load at time $t_1$;

determining with the processor the apparent change in weight $\Delta w_{td}$ of the load, between the time $t_0$ at which the load is subjected to the environment and the time $t_2$ at which the load and environment temperatures reach equilibrium, induced solely by the temperature differential between the load and the environment, from the measured load weights $w_0$ and $w_1$; and generating a signal with the processor representative of the change in weight $\Delta w_{td}$.

13. A method of compensating for load/environment temperature differential-induced measured load weight error comprising the steps of:

providing a load having a load temperature $T_L$;

providing an environment having an environment temperature $T_E$, different from the load temperature;

providing a processor;

providing a weighing device;

subjecting the load to the environment at time $t_0$;

measuring with the weighing device the weight $w_0$ of the load at time $t_0$;

measuring with the weighing device the weight $w_1$ of the load at time $t_1$;

measuring with the weighing device the weight $w_2$ of the load at time $t_2$;

determining with the processor the apparent change in weight $\Delta w_{td}$ of the load, between the time $t_0$ at which the load is subjected to the environment and the time $t_3$ at which the load and environment temperatures reach equilibrium, induced solely by the temperature differential between the load and the environment, from the measured load weights $w_1$ and $w_2$; and generating a signal with the processor representative of the change in weight $\Delta w_{td}$.

14. A method of determining the binder content of a sample of building material by combusting the binder from the balance of the sample in a furnace, including compensating for sample/furnace temperature differential-induced measured sample weight error, comprising the steps of:

providing a sample of building material having a sample temperature $T_s$ and containing an amount of binder to be determined;

providing a furnace having a furnace temperature $T_F$, different from the sample temperature;

providing a processor;

providing a weighing device;

placing the sample into the furnace at time $t_0$;

measuring with the weighing device the initial weight $w_0$ of the sample at time $t_0$;

measuring with the weighing device the weight $w_1$ of the sample at time $t_1$;

determining with the processor the apparent change in weight $\Delta w_{td}$ of the sample, between the time $t_0$ at which the sample is placed into the furnace and the time $t_2$ at which the sample and furnace temperatures reach equilibrium, induced solely by the temperature differential between the sample and the furnace, from the measured sample weights $w_0$ and $w_1$;

combusting with the furnace substantially entirely all the binder from the sample;

measuring with the weighing device the residual weight $w_3$ of the sample at time $t_3$;

subtracting with the processor the temperature differential-induced sample weight change $\Delta w_{td}$ from the difference between the sample residual weight $w_3$ and the sample initial weight $w_0$ to produce a compensated sample weight change $\Delta w_c$ indicative of the sample binder content; and generating a signal with the processor representative of the compensated sample weight change $\Delta w_{td}$.

15. A method of determining the binder content of a sample of building material by combusting the binder from the balance of the sample in a furnace, including compensating for sample/furnace temperature differential-induced measured sample weight error, comprising the steps of:

providing a sample of building material having a sample temperature $T_s$ and containing an amount of binder to be determined;

providing a furnace having a furnace temperature $T_F$, different from the sample temperature;

providing a processor;

providing a weighing device;

placing the sample into the furnace at time $t_0$;

measuring with the weighing device the initial weight $w_0$ of the sample at time $t_0$;

measuring with the weighing device the weight $w_1$ of the sample at time $t_1$;

measuring with the weighing device the weight $w_2$ of the sample at time $t_2$;

determining with the processor the apparent change in weight $\Delta w_{td}$ of the sample, between the time $t_0$ at which the sample is placed into the furnace and the time $t_3$ at which the sample and furnace temperatures reach equilibrium, induced solely by the temperature differential between the sample and the furnace, from the measured sample weights $w_1$ and $w_2$;

combusting with the furnace substantially entirely all the binder from the sample;

measuring with the weighing device the residual weight $w_4$ of the sample at time $t_4$;

subtracting with the processor the temperature differential-induced sample weight change $\Delta w_{td}$ from the difference between the sample residual weight $w_4$ and the sample initial weight $w_0$ to produce a compensated sample weight change $\Delta w_c$ indicative of the sample binder content; and generating a signal with the processor representative of the compensated sample weight change $\Delta w_{td}$.

16. Apparatus for determining the binder content of a sample of building material by weighing the sample before combustion, combusting the binder from the balance of the sample, and weighing the sample after combustion, comprising:

a furnace for insertion of the sample thereinto and for combusting substantially entirely all the binder from the sample;

a scale for measuring the weight of the sample in said furnace at discrete time intervals;

means for determining the apparent change in weight of the sample between the time at which the sample is placed into said furnace and the time at which the sample and said furnace temperatures reach equilibrium, induced solely by the temperature differential between the sample and said furnace, from at least two measured sample weights made prior to the time at which the sample and said furnace temperatures reach equilibrium;

said means for determining also for subtracting the change in weight of the sample induced by the temperature differential from the total change in weight of the sample between the time the sample is placed into said furnace and the time at which combustion of the binder is substantially complete to produce a compensated sample weight change indicative of the sample binder content; and means for displaying the binder content.

17. Apparatus for determining the binder content of a sample of building material by weighing the sample before combustion, combusting the binder from the balance of the sample, and weighing the sample after combustion, comprising:

a furnace for insertion of the sample thereinto and for combusting substantially entirely all the binder from the sample;

a scale for measuring the weight of the sample in said furnace at discrete time intervals;

a processor for determining the apparent change in weight of the sample between the time at which the sample is placed into said furnace and the time at which the sample and said furnace temperatures reach equilibrium, induced solely by the temperature differential between the sample and said furnace, from at least two measured sample weights made prior to the time at which the sample and said furnace temperatures reach equilibrium;

said processor also for subtracting the change in weight of the sample induced by the temperature differential from the total change in weight of the sample between the time the sample is placed into said furnace and the time at which combustion of the binder is substantially complete to produce a compensated sample weight change indicative of the sample binder content; and a display for displaying the binder content.

* * * * *

UNITED STATES PATENT AND TRADEMARK OFFICE
CERTIFICATE OF CORRECTION

PATENT NO. : 5,801,337
DATED : September 1, 1998
INVENTOR(S) : Steven C. Peake

Page 1 of 2

It is certified that error appears in the above-identified patent and that said Letters Patent is hereby corrected as shown below:

Column 3, line 56 "$t_0$" should read -- $t_1$ --.

Column 4, line 54 "induce" should read -- induced --.

Column 5, line 60 "to provided" should read -- to provide --.

Column 6, line 38 "empirocally" should read -- empirically --.

Column 7, line 53 "providing processor" should read

--providing a processor --.

Column 9, line 18 "providing processor" should read

-- providing a processor --.

Column 9, line 19 "providing weighing" should read

-- providing a weighing --.

UNITED STATES PATENT AND TRADEMARK OFFICE
CERTIFICATE OF CORRECTION

PATENT NO. : 5,801,337
DATED : September 1, 1998
INVENTOR(S) : Steven C Peake

It is certified that error appears in the above-identified patent and that said Letters Patent is hereby corrected as shown below:

Column 10, line 53 "substracting" should read -- subtracting --

Signed and Sealed this

Twenty-third Day of February, 1999

Attest:

Attesting Officer

Q. TODD DICKINSON

Acting Commissioner of Patents and Trademarks